United States Patent [19]
Crandell et al.

[11] 3,951,152
[45] Apr. 20, 1976

[54] CRYOSURGICAL PROBE

[75] Inventors: William H. Crandell, Lexington, Mass.; Wayne F. Lisenbee, Simi; Keith E. Nelson, Rolling Hills Estates, both of Calif.

[73] Assignee: Dynatech Corporation, Cambridge, Mass.

[22] Filed: Feb. 14, 1975

[21] Appl. No.: 550,124

Related U.S. Application Data

[62] Division of Ser. No. 475,787, June 3, 1974, Pat. No. 3,910,278.

[52] U.S. Cl. .............................. 128/303.1; 62/293
[51] Int. Cl.² ......................................... A61B 17/36
[58] Field of Search .................... 62/293; 128/303.1

[56] References Cited
UNITED STATES PATENTS

| | | | |
|---|---|---|---|
| 3,502,081 | 3/1970 | Amoils | 128/303.1 |
| 3,524,446 | 8/1970 | Crump | 128/303.1 |
| 3,548,829 | 12/1970 | Reynolds | 128/303.1 |
| 3,575,176 | 4/1971 | Crump | 128/303.1 |

*Primary Examiner*—Channing L. Pace
*Attorney, Agent, or Firm*—Cesari & McKenna

[57] ABSTRACT

A small, self-contained, disposable cryosurgical probe has a pencil-like housing with a refrigerant-containing cartridge in the housing and a hollow tip projecting from the housing. A small diameter capillary tube has one end in the housing opposite the cartridge and its other end extending into the tip with the intervening length of the tube formed into a multi-turn coil. The refrigerant is conducted from the cartridge through the tube to the probe tip and the temperature of the refrigerant is stabilized so as to maintain a substantially uniform mass flow rate of refrigerant through the tube to the tip.

3 Claims, 4 Drawing Figures

U.S. Patent   April 20, 1976   3,951,152
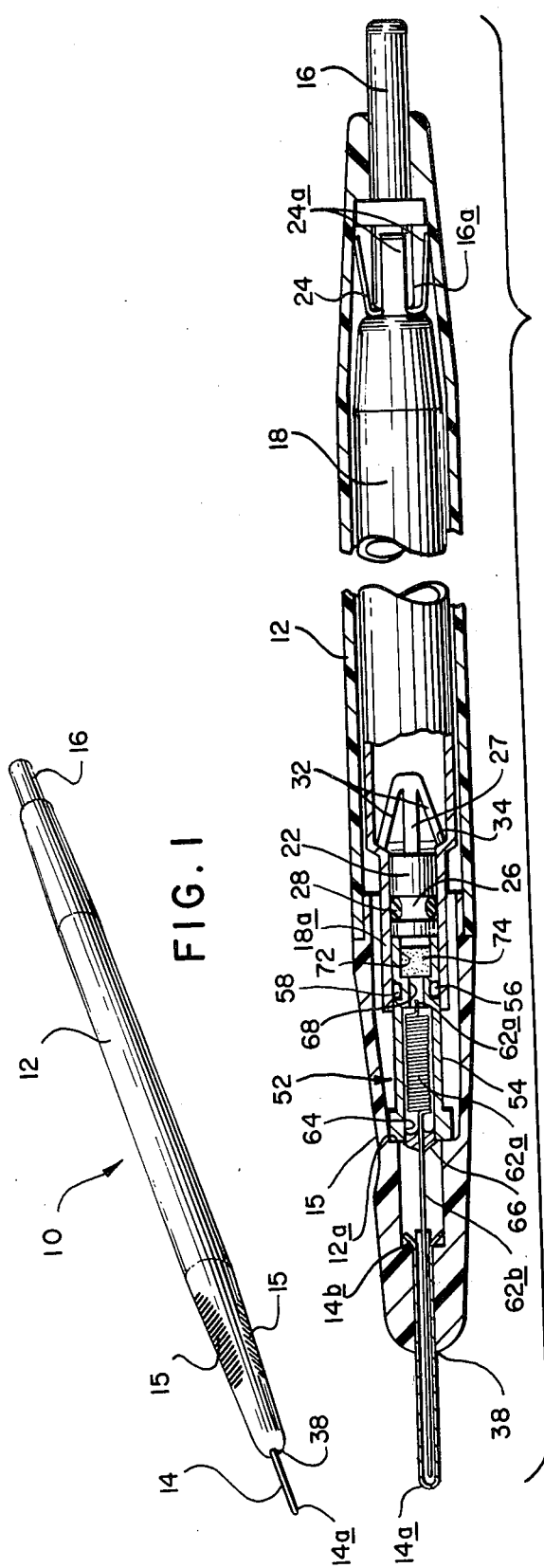
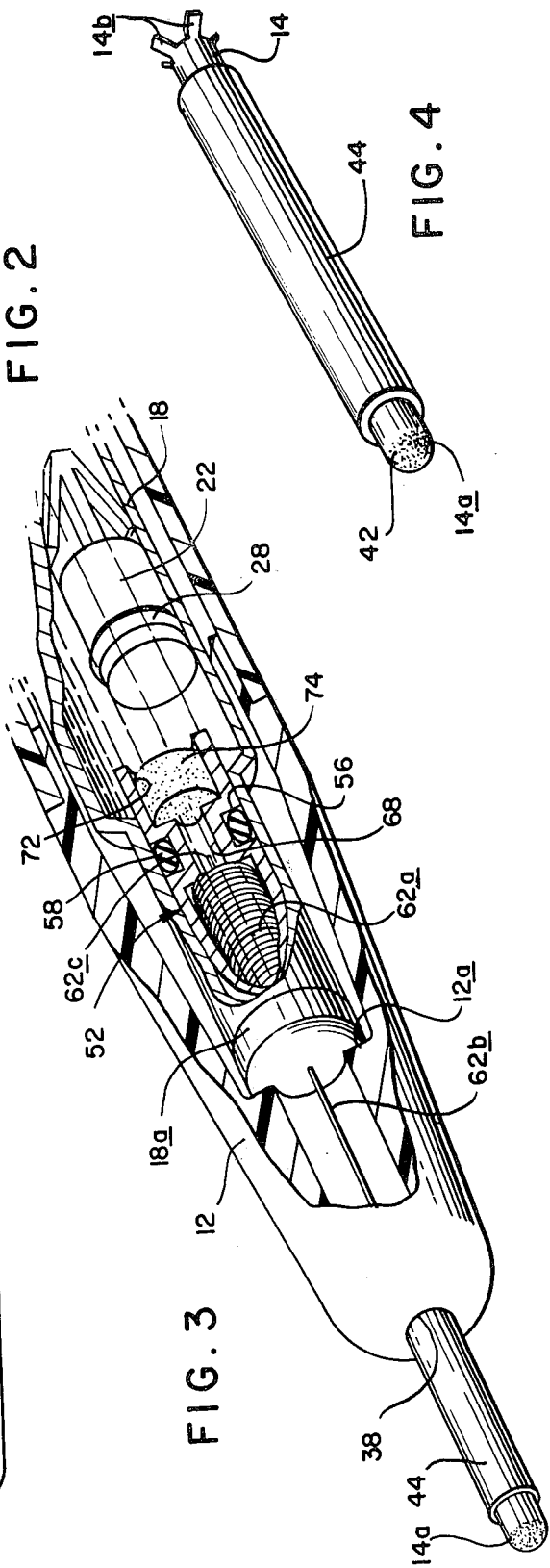

CRYOSURGICAL PROBE

This is a division, of application Ser. No. 475,787 filed June 3, 1974, now U.S. Pat. No. 3,910,278 dated Oct. 7, 1975.

There are in use today some self-contained probes which do not require a separate fluid supply. Basically, these units consist of a housing containing a reservoir of a suitable refrigerant such as Freon gas, maintained as a liquid under high pressure. When it is desired to use the probe, a diaphragm in the wall of the reservoir is ruptured, allowing the refrigerant therein to flow into a chamber where the Freon evaporates and in the process cools itself and the inner end of the probe tip inside the chamber. The working end of the tip projecting from the chamber is then cooled by thermal conduction.

While these conventional disposable probes do work, their operation is not entirely satisfactory. Their main problem stems from the fact that the working end of the probe tip is not cooled directly by the refrigerant but rather by thermal conduction along the entire length of the tip. Since the cross-section of the tip is quite small, especially in the case of ophthalmic probes, it takes ten seconds or more to cool the tip end to the requisite working temperature of, say, −30°C.

Some prior probes are also disadvantaged in requiring a relatively large supply of refrigerant. This makes the probe body excessively large, e.g., one inch in diameter and four inches long, and therefore unwieldy and difficult to manipulate over the patient's eye.

Other prior self-contained probes are overly expensive and have a relatively short operating time which may encourage the doctor to rush surgical procedures. Still other probes sometimes forcefully discharge foreign material from the punctured diaphragm which can cause injury to the doctor or the patient. All of these factors have militated against the wider use and acceptance of self-contained disposable cryosurgical probes.

SUMMARY OF THE INVENTION

The present invention aims to provide a self-contained cryosurgical probe which is small, compact and easy to handle.

A further object of the invention is to provide a probe of this type which, when activated, brings the probe tip to the operating temperature in a few seconds.

Another object of the invention is to provide a self-contained ophthalmic probe which can maintain its working temperature for a relatively long time.

Yet another object of the invention is to provide a probe of this general type which is relatively inexpensive to make and which therefore may be thrown away after each operation.

A further object of the invention is to provide a self-contained probe which though having a very small diameter working tip is able to develop and hold a relatively large ice-ball at its working temperature.

Still another object of the invention is to provide a self-contained probe which can be recharged and reused.

Still another object is to provide a disposable cryosurgical ophthalmic probe having a relatively long shelf life.

Another object of the invention is to provide a self-contained probe of this type whose refrigerant supply can be conserved following actuation of the probe to accommodate temporary interruptions in the surgical procedure.

Other objects will in part be obvious and will in part appear hereinafter.

The invention accordingly comprises the features of construction, combination of elements and arrangement of parts which will be exemplified in the following detail description, and the scope of the invention will be indicated in the claims.

In general, the present cryosurgical probe consists of a thin, pencil-like housing containing a cylindrical cartridge filled with a suitable pressurized refrigerant such as liquid Freon. The refrigerant is maintained at room temperature and is retained within the cartridge by a special removable plug, or other fluid tight seal, recessed into the end of the cartridge, to be described in detail later.

The probe tip is positioned in the end of the housing opposite that plug. It consists of a relatively small diameter tube having one end secured in the end of the housing and projecting an appreciable distance from the housing, the exterior end of the tube being closed.

A cylindrical plunger is positioned between the plug and the probe tip. The plunger projects into the end of the cartridge somewhat and a sliding seal is provided between the plunger and the cartridge wall. A long length of capillary tubing is coiled up inside the plunger. One end of the tubing communicates with the end of the plunger opposite the plug, and the opposite end of the tubing projects from the other end of the plunger into the hollow probe tip almost to its closed end.

The refrigerant cartridge is mounted in the housing so that it can be moved along the housing axis toward the plunger by means of a push-button installed in the end of the housing remote from the tip. When the button is depressed, the cartridge is urged toward the plunger which thereupon pushes the plug into the cartridge until the seal between the plug and the cartridge wall is broken. The Freon then flows into the capillary tube within the plunger and issues from the end thereof adjacent the working end of the probe tip. As it leaves the capillary tube, the Freon evaporates and expands and become cold in the process thereby directly cooling the probe tip. The Freon exhausts as a gas from the tip through the spaces between the housing and the plunger and cartridge walls, and leaves the probe through the crack around the push-button.

The working end of the probe tip is brought to operating temperature quite quickly because the cooling process does not depend upon thermal conduction along the tip to cool the tip end. Rather, the Freon is delivered directly to the probe tip and thus cooling takes place right at the working end of the tip.

The probe is able to operate consistently for a relatively long period of time, e.g., 3–5 minutes, on the moderate amount of refrigerant contained inside the cartridge e.g., 3cc, of which 2.3cc is liquid at room temperature, because the probe maintains two phase flow of Freon through the capillary tube to the probe tip. In other words, the Freon flows through the capillary tube as a saturated vapor and liquid so that cooling at the tip is caused primarily by evaporation of the refrigerant right at the tip.

This two phase flow is achieved by isolating and insulating the Freon flowing through the capillary tube from the cold gas exhausting from the tip, thereby inhibiting regenerative cooling of the incoming refrigerant. Although it may be accomplished in other ways, the isolation is accomplished by bringing the room temperature liquid Freon into intimate contact with the capillary tube coiled inside the plunger. Thus when the probe is activated by depressing the push-button, liquid Freon is allowed to flow down into the plunger so that the capillary tube therein is bathed in the room temperature liquid. Since the specific volume of the fluid flowing to the tip is kept relatively high in this manner, the probe tip can be maintained at its −30°C. working temperature for as long as 3 to 5 minutes, quite enough time to complete a cataract extraction operation.

On the other hand, if the refrigerant flowing through the capillary tube to the tip is not isolated in this fashion from the cold exhaust gas, the incoming refrigerant would be cooled so that it would flow to the tip primarily in its liquid phase. The flow of the liquid refrigerant to the tip would then be significantly more than required to offset the heat load upon the tip from without, and the tip and chamber would be flooded with excess refrigerant which would therefore be wasted.

If necessary, the doctor can conserve the refrigerant supply in the present probe if he should activate the probe prematurely or requires a brief interruption in the operation. More particularly he may point the probe tip upwards causing the liquid refrigerant to drain from the plunger. The incoming Freon is now in its gaseous phase so that its mass rate of consumption drops. If the doctor now points the tip downward again, the incoming Freon becomes a combination of a saturated vapor and liquid again and the tip cools to its working temperature in two or three seconds, whereupon the operation can be resumed.

Even though the subject probe has a very small diameter tip, only on the order of 0.062 in. its cooling capacity is such that it can form an iceball as large as 3.5mm in diameter. Since the tip presents so little surface area, the ice-balls formed thereon sometimes have a tendency to fall off. Accordingly, the working end of the tip is intentionally abraded or roughened to increase the adherence of the iceball to the tip.

The subject probe is intended primarily to be a disposable item because its cost is so low. However, provision can be made for replacing the Freon cartridge so that the probe can be reused. All of the probe parts are able to withstand ethylene oxide gas so that the probe can be resterilized prior to each use. Also provision can be made for stopping the exhaust of refrigerant from the probe in order to build up a back pressure at the probe tip to cause the probe tip to defrost. This feature facilitates detachment of the probe from tissue. These aspects of the probe will be described in greater detail later.

With its advantages of small size, light weight rapid freezing following actuation, and long running time, the present probe should prove to be an invaluable surgical instrument particularly for delicate eye operations such as a cataract removal or removal of foreign material from the vitreous humor.

BRIEF DESCRIPTION OF THE DRAWING

For a fuller understanding of the nature and objects of the invention, reference should be had to the following description taken in connection with the accompanying drawing, in which:

FIG. 1 is a perspective view of a self-contained cryosurgical ophthalmic probe made in accordance with this invention;

FIG. 2 is a sectional view on a larger scale of the FIG. 1 probe before actuation;

FIG. 3 is a fragmentary view with parts broken away on a still larger scale showing elements of the probe in greater detail after the probe is activated, and FIG. 4 is a perspective view on an even larger scale showing the probe tip in greater detail.

DESCRIPTION OF THE PREFERRED EMBODIMENT

Referring to FIG. 1 of the drawing, the probe shown generally at 10, is comprised of a pencil-like plastic housing 12 approximately 5.5 inches long and 0.4 inch in outside diameter. A tubular tip 14 projects from the lower end of the housing. The working end of the tip at 14a is closed. Shaped and roughened finger engaging surfaces 15 are provided on the outside of housing 12 near the tip 14.

Probe 10 is activated by depressing a push-button 16 located at its end remote from tip 14. In two to three seconds following depression of button 16, the probe tip 14a becomes cooled to the desired working temperature, e.g. −30°C. In normal use, the tip 14a will remain at that temperature for at least three minutes which is ample time to complete a cataract extraction procedure even with complications.

Following activation of the probe, freezing at the tip 14a can be interrupted temporarily by orienting the probe so that the tip points upward. The tip will then re-freeze when the probe is returned to its downward orientation. This feature permits the doctor to extend the effective running time of the probe should he activate it prematurely or encounter some reason for briefly delaying a surgical procedure.

Turning now to FIG. 2, housing 12 contains a cylindrical metal cartridge 18 containing a supply of refrigerant, in this case liquid Freon, under a suitable pressure of, say, 75 psi at room temperature (72°F). Cartridge 18 is charged with Freon, say, by way of its necked-down end 18a. That end of the cartridge is then sealed off, for example, by means of a recessed plug 22. The other end of cartridge 18 is positioned inside the housing 12 opposite the inner end 16a of button 16.

Cartridge 18 is dimensioned so that it can shift axially in housing 12 when button 16 is depressed. Furthermore, provision is made for latching the cartridge in its shifted position. This latch can be a latching arrangement such as is found in conventional ballpoint pens, or it can be as shown in FIG. 2, a stamped metal +-shaped claw 24 having resilient arms 24a which dig into the inside wall of housing 12 and resist the return of the cartridge to its original position before button 16 was depressed.

Plug 22, which seals cartridge 18, is generally cylindrical and is provided with a circumferential groove 26, midway along its length, in which seats an O-ring seal 28. After the cartridge 18 is charged with Freon, the plug 22 is inserted to seal off its end 18a. The plug is retained in position despite the 75 psi charging pressure in the cartridge by a pair of flexible, resilient arms 32 supported by a stem 27 projecting from the end of plug 22 inside the cartridge. These arms step out laterally when the plug is inserted and engage behind the shoulder 34 formed where the necked-down cartridge portion 18a begins. When the plug 22 is properly seated, it is recessed somewhat into cartridge portion 18a, as is best seen in FIG. 2.

The probe tip 14 consists of a cylindrical stainless steel tube 0.062 inch in outside diameter and extends 0.5 inch from the housing. One end of the tube extends into the housing through an opening 38 provided therefor, and is secured there by any commercial means. The exposed end of the tube corresponding to the working tip end 14a is closed.

Turning for a moment to FIG. 4, the inner end of tip 14a is intentionally slit to form four small tabs 14b, which splay out and resiliently engage the inside wall of the housing to prevent the tip from rotating and translating relative to housing 12. Although some such rotation can be tolerated in the case of a straight tip, it causes inconvenience when the tip is curved. This is because downward pressure on the probe would then apply a torque to the tip which might cause the tip to rotate the working end 14a away from the tissue being frozen.

The closed end of the probe tip at 14a is textured or roughened as best seen at 42 in FIG. 4. This texturing increases the surface area at 14a and provides minute indentations to which an iceball formed on the end of the tip can adhere. If the tip is not textured in this way, an iceball formed thereat might tend to fall off because the diameter of the tip is so small, and such little contact area exits between the tip and the iceball.

Also, to localize the point on the tip 14 where tissue can adhere, a silicone sleeve 44 is shrunk fit onto the tip covering it except for its working end 14a.

Referring again to FIG. 2, positioned between the cartridge plug 22 and the inner end of tip 14 is a plunger assembly shown generally at 52. Assembly 52 includes a generally cylindrical tube 54 having a circumferential groove 56 in its outer wall for accommodating O-ring seal 58. The tube 54 is arranged so that it slidably fits inside cartridge portion 18a with the O-ring providing a fluid-tight seal between the tube and the cartridge wall in the presence of the pressurized refrigerant.

During the shelf-life of the probe, one end of the plunger tube 54 is positioned within cartridge portion 18a as shown in FIG. 2, while its other end butts against a shoulder 12a formed in housing 12 adjacent tip 14 which prevents movement of the plunger toward the tip.

Plunger 52 also supports a long, small-diameter No. 32 gauge stainless steel capillary tube 62. The tube has an inside diameter of 0.004 inch and is on the order of 1 foot in length. Most of the tube is contained as a 0.3 inch long 0.117 inch diameter coil 62a seated in a bore 64 in the outer end of tube 54. A straight capillary tube segment 62b extends from the outer end of the coil into probe tip 14 almost to its working end 14a. A suitable epoxy potting compound 66 seals off the open outer end of bore 64.

A second straight tubing segment 62c extends from the inner end of coil 62a into an axial passage 68 leading from bore 64 to a second bore 72 at the other end of plunger tube 54.

A plug 74 of a suitable filter material such as porous polyethylene is inserted into bore 72 adjacent to the open inner end of the capillary tube 62 to prevent any foreign matter from entering and possibly clogging the tube.

Referring now to FIGS. 2 and 3, when it is desired to activate probe 10, the button 16 is depressed. This movement of the button shifts cartridge 18 axially within housing 12 and urges it toward plunger 52 whose position is fixed. The inner end of the plunger is pressed against plug 22 and pushes the plug sufficiently into the cartridge to break the seal between the plug and the cartridge wall, thereby releasing the pressurized Freon in the cartridge as shown in FIG. 3. The Freon flows through the filter plug 74 and the capillary tube 62 and issues from the tube end inside tip 14a. Very little work is done by the Freon cooling the cartridge 18. Rather, the refrigerant undergoes both expansion and evaporation cooling in the cavity right at tip end 14a, so that the tip is brought to its working temperature of at least −30°C in only 2 or 3 seconds. The refrigerant exhausts as a cold gas from the tip through the space between the housing wall and cartridge 18 and plunger 52 and leaves the probe through the circular crack in the housing around the actuating button 16.

As best seen in FIG. 3, liquid Freon still at room temperature is free to flow through the space between the wall of passage 68 and tubing segment 62c so that it bathes the capillary tube coil inside the bore. Thus the liquid serves as an insulating and isolating blanket between coil 62a and the cold gas exhausting from tip 14. Consequently, there is little if any regenerative cooling of the incoming Freon with the result that two phase flow is maintained rather than all liquid flow during the entire operating time of the probe. This factor gives the probe a relatively long running time, e.g. 3 to 5 minutes, even though the cartridge 18 has a relatively small volume, e.g., 3 cc, and the capillary tube 62 has a bore which is large enough (e.g., 0.004 inch) so that plugging is not a problem. In this connection we should mention that if the refrigerant supply has a volume much more than 12cc, the overall probe becomes unduly large and unwieldy and therefore difficult to use.

If only liquid flows through the capillary tube 62 a relatively large supply of refrigerant is required, to provide cooling for three minutes, thus necessitating a much larger cartridge. This, in turn, would make the overall probe as large and unwiedly as some prior self-contained probes. On the other hand, if the refrigerant flows to the probe tip only as a gas, cooling occurs primarily by the Joule Thompson effect and expansion rather than by the more efficient evaporation phenonemon so that the cooling of the probe tip is not sufficient to overcome the heat load imposed on the probe at normal room temperatures.

The small lightweight self-contained disposable probe with which we are concerned here has a limited refrigerant supply which must maintain the probe tip at the required low temperature for the required time. To make maximum use of this limited supply, the refrigerant is delivered right to the working end of the probe tip where the tip end is cooled primarily by the process of evaporation which is a most efficient mode of cooling.

Also, since the mass flow rates of the refrigerant are drastically different depending upon whether the refrigerant is in its liquid or gaseous phase (the ratio is at least 5 to 1), the temperature of the liquid refrigerant flowing to the tip is stabilized so that the refrigerant enters the chamber inside the tip as a two-phase fluid when the probe is activated initially and during its entire operating time. In other words, the point in the capillary tube at which the super heated refrigerant boils or evaporates is kept more or less the same so that the mass flow rate of the refrigerant to the tip also remains the same and is predictable from probe to probe. This flow rate is sufficient immediately upon actuation of the probe to cool the tip to a temperature low enough to cause the tip to adhere to tissue in a few seconds. Further the flow rate does not increase materially due to regenerative cooling of the incoming Freon by the cold gas exhausting from the probe and does not decrease appreciably due to a normal heat load on the probe tip.

The point in the capillary tube at which the liquid Freon boils cannot be determined exactly. Based on empirical results, if boiling occurs too near the beginning of the tube, the mass flow rate of the refrigerant is too low to sustain a low enough tip temperature in a room temperature environment. On the other hand if it occurs too near to the end of the tube, the mass flow rate is excessively high so that while the tip is cooled quite adequately, all of the Freon in the cartridge is used up too fast so that the probe does not have a three minute operating time.

The best estimate is that boiling should occur approximately 80 percent along the length of the capillary tube 62 for best results in terms of tip temperature and operating time.

In the present probe, the temperature of the incoming Freon is stabilized by isolating and insulating it from the cold gas exhausting from the probe tip. This exhaust gas would otherwise cool the incoming refrigerant as the probe continues to run, thereby shifting the point in the tube 62 at which boiling occurs toward the end of the tube. This in turn would increase the mass flow rate of the refrigerant and shorten the running time of the probe. While the means of isolation may take different forms, it is accomplished here conveniently by bathing the coil 62a in room temperature liquid Freon from cartridge 18. It is also feasible to isolate the tube by potting it in a thermally insulating material.

With the present probe, the supply of refrigerant can be conserved once the probe has been activated. If the doctor is not quite prepared to work on the patient for one reason or another after he depresses button 16, he can orient the probe so that its tip end 14a points upwards. The liquid Freon bathing coil 62a then flows back into cartridge and only gas is available to flow to the tip 14a and its rate of consumption is much less than it would be if it flowed as a two phase satuated vapor - liquid system. In fact, the flow of Freon as a gas can continue as long as 5 or 6 minutes. This means that if the doctor holds the probe upright for even as long as a minute or more and then starts or resumes a cataract removal operation by pointing the probe downwards, the tip 14a will reach its working temperature in two or three seconds and ample Freon will still remain in cartridge 18 to run the probe for 2 to 3 minutes which is ample time to complete a cataract removal procedure even if further complications arise.

Thus despite its small, slim profile, the present probe contains the requisite amount of refrigerant to maintain the probe at the proper operating temperature for the normal time required for a cataract removal operation or a vitreous removal procedure. The probe is lightweight so that it can be manipulated easily and precisely by the doctor, yet its cost of manufacture is low enough so that the unit can be considered disposable.

In situations where it is necessary to store the fully charged probe for a long period before use, it may be desirable to seal cartridge 18 by means of a brass diaphragm instead of a plug 22. In this event the inner edge of the plunger tube 54 may be sharpened so that when the button 16 is depressed, the sharpened edge cuts through the diaphragm and releases the refrigerant.

Also it may sometimes be preferable to re-use the probe, in which case the housing 12 would be comprised of two sections threaded together. When the refrigerant in cartridge 18 is expended, the housing sections would be taken apart and the cartridge 18 pulled away from the plunger 52 which would be retained in the lower end of the housing. Then a new capsule 18 would be inserted down on the plunger after which the housing sections would be screwed together. Following re-sterilization, the probe would then be ready for re-use.

It may also be desirable to be able to heat the probe tip to facilitate its detachment from tissue. This can be accomplished in the present probe by providing a flexible seal over the button 16 in the upper end of the housing which would permit the button to be depressed, yet prevent gas from exhausting through the crack between the button and the housing. Then a separate valved exit port is provided within the housing which would remain open when it is desired to cool the probe tip. When the surgical procedure is completed and it is desired to release the tip from the tissue, this valve would be closed resulting in a back pressure build-up inside the probe tip which warms the tip sufficiently to melt the tissue contacted by the tip.

It will thus be seen that the objects set forth above among those made apparent from the preceding description are efficiently attained and since certain changes may be made in the above constructions without departing from the scope of the invention, it is intended that all matter contained in the above description or shown in the accompanying drawing should be interpreted as illustrative and not in a limiting sense.

It is also to be understood that the following claims are intended to cover all of the generic and specific features of the invention herein described.

We claim:

1. The method of cooling a disposable cryosurgical probe having a small diameter hollow tip comprising the steps of
   A. flowing a pressurized liquid refrigerant at room temperature through a capillary tube having an end in the probe tip,
   B. bathing the outside of said capillary tube in the room temperature liquid refrigerant so that refrigerant flows through the capillary tube as a two-phase fluid having a relatively high specific volume, and
   C. discharging said refrigerant fluid from the end of the capillary tube into the probe tip so that evaporation cooling takes place right at the probe tip.

2. The method defined in claim 1 and including the additional step of orienting the probe so that refrigerant flows to the tip solely as a gas at a relatively low mass flow rate so as to conserve a given supply of refrigerant in the probe.

3. The method of sustaining cooling of the hollow tip of a small disposable cryosurgical probe having a self-contained refrigerant supply with a volume less than 12cc comprising the steps of
   A. flowing liquid refrigerant into the probe tip at a mass flow rate such that the refrigerant evaporates inside the tip and thereby cools the tip directly to a temperature in a room temperature below 0°C environment in less than 6 seconds, and
B. continuing the refrigerant flow for at least 1.5 minutes.

* * * * *

UNITED STATES PATENT OFFICE
CERTIFICATE OF CORRECTION

Patent No. 3,951,152     Dated April 20, 1976

Inventor(s) William H. Crandell et al

It is certified that error appears in the above-identified patent and that said Letters Patent are hereby corrected as shown below:

Please change column 8, line 68 (last line in column), to read as follows:

temperature below 0°C in a room temperature

Signed and Sealed this

Sixth Day of July 1976

[SEAL]

Attest:

RUTH C. MASON
*Attesting Officer*

C. MARSHALL DANN
*Commissioner of Patents and Trademarks*